United States Patent [19]

Saunders et al.

[11] Patent Number: 5,066,792

[45] Date of Patent: Nov. 19, 1991

[54] GENE PROBE FOR DETECTION OF SPECIFIC HUMAN LEUKEMIAS

[75] Inventors: Grady F. Saunders; Wendy M. Mars, both of Houston, Tex.

[73] Assignee: Board of Regents University of Texas, Austin, Tex.

[21] Appl. No.: 279,451

[22] Filed: Dec. 2, 1988

Related U.S. Application Data

[63] Continuation-in-part of Ser. No. 94,099, Sep. 4, 1987, Pat. No. 4,857,466, which is a continuation of Ser. No. 655,942, Sep. 28, 1984, abandoned.

[51] Int. Cl.$^5$ .................. C07H 21/04; C12Q 1/68
[52] U.S. Cl. ........................... 536/27; 435/6; 435/91; 435/172.3; 436/501; 436/813; 935/4; 935/78
[58] Field of Search ............ 435/6, 91, 172.3; 436/501, 813; 536/27; 935/4, 78

[56] References Cited

U.S. PATENT DOCUMENTS

| | | | |
|---|---|---|---|
| 4,167,556 | 9/1979 | Selhub | 424/1 |
| 4,192,917 | 3/1980 | Zurawski, Jr. | 435/236 |
| 4,273,757 | 6/1981 | Selhub et al. | 424/1 |
| 4,358,535 | 11/1982 | Falkow et al. | 435/5 |
| 4,394,443 | 7/1983 | Weissman et al. | 435/6 |
| 4,399,216 | 8/1983 | Axel et al. | 435/6 |
| 4,411,994 | 10/1983 | Gilbert et al. | 435/71 |
| 4,414,150 | 11/1983 | Goeddel | 260/112.5 R |
| 4,424,201 | 1/1984 | Valinsky et al. | 424/3 |
| 4,431,740 | 2/1984 | Bell et al. | 435/253 |
| 4,464,465 | 8/1984 | Lostrom | 435/68 |
| 4,542,096 | 9/1985 | Leder | 435/6 |
| 4,543,252 | 9/1985 | Lehrer et al. | 514/12 |
| 4,562,159 | 12/1985 | Shafritz | 436/501 |
| 4,599,305 | 7/1986 | Witte et al. | 435/7 |
| 4,659,692 | 4/1987 | Lehrer et al. | 514/12 |
| 4,681,840 | 7/1987 | Stephenson et al. | 435/6 |
| 4,701,409 | 10/1987 | Croce | 435/6 |
| 4,705,777 | 11/1987 | Lehrer et al. | 514/12 |

FOREIGN PATENT DOCUMENTS

| | | |
|---|---|---|
| 0162161 | 11/1985 | European Pat. Off. |
| 0275194 | 7/1988 | European Pat. Off. |
| WO88/04666 | 6/1988 | PCT Int'l Appl. |
| WO89/11291 | 11/1989 | PCT Int'l Appl. |

OTHER PUBLICATIONS

Mars et al., "Preferentially Expressed Genes in Chronic Myelogenous Leukemia", Blood (1985).
Mars et al., "Localization of an Abundant Myeloid-Related Sequence", Acta Haematologica 78:11 (1987).
Mars et al., "Localization of an Abundant Myeloid mRNA to Individual Leukocytes in Mixed Cell Populations", Leukemia 1:167 (1987).
Mars et al., "A Myeloid-Related Sequence that Localizes to Human Chromosome 8q21.1-22", Blood 71:1713 (1988).
Ganz et al., Eur. J. Hematol., 44:1-8 (1990).
Alberts et al., Molecular Biology of the Cell p. 409.
Lewin, "Gene Expression"; vol. 2: Eucaryotic Chromosomes (1980), p. 727.
Lewin, "Genes", (1983), pp. 297-298.
Mars, "Gene Expression in Chronic Myelogenous Leukemia"(1986), Ph.D. Dissertation for Univ. of Texas.
Srinivasan et al., "Abelson Murine Leukemia Virus: Molecular Cloning of Infectious Integrated Proviral (List continued on next page.)

Primary Examiner—Robert A. Wax
Assistant Examiner—Ardin H. Marschel
Attorney, Agent, or Firm—Arnold, White & Durkee

[57] ABSTRACT

Gene probes containing genetic sequences that code for proteins which are phenotypically characteristic of certain leukemias, such as chronic myelogenous leukemia, can be prepared from RNA of a person having that disease. A useful probe has been found which comprises a sequence localized to chromosome 8, the sequence being complementary to a mRNA that is characteristically present in high abundance in chronic myelogenous leukemia cells. The gene probes can be used in diagnostic hybridization tests with RNA or a patient to be diagnosed.

3 Claims, 2 Drawing Sheets

```
XXX XXX XXX XXX XCT ATA GAA GAC CTG GGA CAG AGG ACT GCT GTC TGC CCT CTC TGG -  57
            (ile glu asp leu gly gln arg thr ala val cys pro leu trp TCA CCC TGC CTA GCT AGA GGA TCT GTG ACC CCA GCC ATG AGG ACC CTC GCC ATC CTT - 114
ser pro cys leu ala arg gly ser val thr pro ala)MET arg thr leu ala ile leu GCT GCC ATT CTC CTG GTG GCC CTG CAG GCC CAG GCT GAG CCA CTC CAG GCA AGA GCT - 171
ala ala ile leu leu val ala leu gln ala gln ala glu pro leu gln ala arg ala GAT GAG GTT GCT GCA GCC CCG GAG CAG ATT GCA GCG GAC ATC CCA GAA GTG GTT GTT - 228
asp glu val ala ala ala pro glu gln ile ala ala asp ile pro glu val val val TCC CTT GCA TGG GAC GAA AGC TTG GCT CCA AAG CAT CCA GGC TCA AGG AAA AAC ATG - 285
ser leu ala trp asp glu ser leu ala pro lys his pro gly ser arg lys asn MET GCC TGC TAT TGC AGA ATA CCA GCG TGC ATT GCA GGA GAA CGT CGC TAT GGA ACC TGC - 342
ala cys tyr cys arg ile pro ala cys ile ala gly glu arg arg tyr gly thr cys ATC TAC CAG GGA AGA CTC TGG GCA TTC TGC TGC TGA GCT TGC AGA AAA AGA AAA ATG - 399
ile tyr gln gly arg leu trp ala phe cys cys *

AGC TCA AAA TTT GCT TTG AGA GCT ACA GGG AAT TGC TAT TAC TCC TGT ACC TTC TGC - 456

TCA ATT TCC TTT CCT CAT CCC AAA TAA ATG CCT TGG TAC AAG                      - 498
```

OTHER PUBLICATIONS

DNA", Proc. Natl. Acad. Sci., U.S.A., 78:2077 (1981).

Wang et al., "Cellular RNA Homologous to the Abelson Murine Leukemia Virus Transforming Gene: Expression and Relationship to the Viral Sequence", Molec. & Cell. Biol. 3:773 (1983).

Wiedemann et al., "Differences Among the Polyadenylated RNA Sequence of Human Leuycocyte Populations: an Approach to the Objective Classification of Human Leukaemias", EMBO Jrnl. 2:9 (1983).

Birnie et al., "A New Approach to the Classification of Human Leukemias: Measurement of the Relative Abundance of a Specific RNA Sequence by Means of Molecular Hybrisization", Lancet (Jan. 29, 1983).

Selsted et al., "Primary Structures of Three Human Neutrophil Defenses", J. Clin. Invest. 76:1436 (1985).

Singh et al., "Structure of Novel Human Granulocyte Peptide with Anti-ACTH Activity", Biochem. & Biopys. Res. Commun. 155:524 (1988).

Selden et al., "Amplified C and c-abl Genes are on the Same Marker Chromosome in K562 Leukemia Cells", Proc. Natl. Acad. Sci. U.S.A. 80:7289 (1983).

Collins et al., "Altered Transcription of the c-abl Oncogene in K-562 and Other Chronic Myelogenous Leukemia Cells", Science 225:72 (1984).

Frazier et al., "Efficient Extraction of RNA from Mammalian Tissue", Molec. and Cell. Biochem. 56:113 (1983).

Munjaal et al., "Isolation and Characterization of Preproinsulin mRNA from Fetal Bovine Pancreatic Islets", Molec. and Cell. Endocrin. 15:51 (1979).

Shtivelman et al., "Fused Transcript of abl and bcr Genes in Chronic Myelogenous Leukaemia", Nature 315:550 (1985).

Srinivasan et al., "Abelson Murine Leukemia Virus: Structural Requirements for Transforming Gene Function", Proc. Natl. Acad. Sci. U.S.A. 79:5508 (1982).

Mars et al., "Identification of Sequences Preferentially Transcribed in Chronic Myelogenous Leukemia", Abstract for Symposium: Cellular and Molecular Biology of Neoplasia, (Oct. 2-6, 1983).

Mars et al., "A Preferentially Transcribed Sequence in Chronic Myelogenous Leukemia and Ph[1]+ Acute Leukemia", (Aug. 1984), Symposium at Penn State.

Mars et al., "A Preferentially Transcribed Sequence in Chronic Myelogenous Leukemia and Ph[1]+ Acute Leukemia"(Sept. 1984).

Saunders et al., "Use of Gene Probes in the Diagnosis and Classification of Myeloid Leukemias", (Nov. 1984), Symposium on the Prevention and Detection of Cancer, 6th International Symposium, Vienna, Austria.

```
XXX XXX XXX XCT ATA GAA GAC CTG GGA CAG AGG ACT GCT GTC TGC CCT CTC TGG -  57
            (ile glu asp leu gly gln arg thr ala val cys pro leu trp TCA CCC TGC CTA GCT AGA GGA TCT GTG ACC ATG CCA GCC ATG AGG ACC CTC GCC ATC CTT - 114
ser pro cys leu ala arg gly ser val thr pro ala)MET arg thr leu ala ile leu GCT GCC ATT CTC CTG GTG GCC CTG CAG GCT GAG CCA CTC CAG GCA AGA GCT - 171
ala ala ile leu leu val ala leu gln ala glu pro leu gln ala arg ala GAT GAG GTT GCT GCA GCC CCG GAG CAG ATT GCA GCG GAC ATC CCA GAA GTG GTT GTT - 228
asp glu val ala ala ala pro glu gln ile ala ala asp ile pro glu val val val TCC CTT GCA TGG GAC GAA AGC TTG GCT CCA AAG CAT CCA GGC TCA AGG AAA AAC ATG - 285
ser leu ala trp asp glu ser leu ala pro lys his pro gly ser arg lys asn MET GCC TGT TAT TGC AGA ATA CCA GCG TGC ATT GCA GAA CGT CGC TAT GGA ACC TGC - 342
ala cys tyr cys arg ile pro ala cys ile ala glu arg arg tyr gly thr cys ATC TAC CAG GGA AGA CTC TGG GCA TTC TGC TGA GCT TGC AGA AAA AGA AAA ATG - 399
ile tyr gln gly arg leu trp ala phe cys cys  *

AGC TCA AAA TTT GCT TTG AGA GCT ACA GGG AAT TGC TAT TAC TCC TGT ACC TTC TGC - 456

TCA ATT TCC TTT CCT CAT CCC AAA TAA ATG CCT TGG TAC AAG                    - 498
```

GENE PROBE FOR DETECTION OF SPECIFIC HUMAN LEUKEMIAS

This patent application is a continuation-in-part of Ser. No. 094,099 filed on Sept. 4, 1987, Now U.S. Pat. No. 4,857,466 which was a continuation of Ser. No. 655,942, filed on Sept. 28, 1984, abandoned.

BACKGROUND OF THE INVENTION

The present invention relates to a method of diagnosing certain leukemias. More specifically, it concerns a method of detecting an RNA sequence which represents a protein or proteins which are phenotypically characteristic of certain leukemias.

Approximately 88% of the patients with clinically typical chronic myelogenous leukemia (CML) have a cytogenetic abnormality known as the Philadelphia chromosome (ph[1]). This aberration has also been reported at a much lower frequency in both acute lymphocytic leukemia (ALL) and acute myelogenous leukemia (AML). Chromosome banding techniques have shown the Ph[1] chromosome to be a shortened chromosome 22 with a break occurring in bands q11. In 92% of the patients with Ph[1]-positive CML, the missing piece of chromosome 22 attaches distally to the long arms of chromosome 9, band q34, in what has been shown to be a reciprocal translocation. Of the Ph[1]-positive variants with a different type of alteration, 4% are known to have complex translocations which again involve chromosome 9.

Specific karyotype abnormalities are also associated with other kinds of malignancies. For example, other types of human and murine leukemias and lymphomas have been correlated with particular cytogenetic changes. Additionally, it is known that certain leukemias with distinct cytogenetic changes display constitutive expression of proteins which are normally regulated during myeloid differentiation. Thus, phenotypic subcategories of leukemia, as defined by karyotype abnormalities, can additionally be defined by protein alterations which in turn may reflect the cellular populations of RNA.

Since preferred treatments differ for different malignancies, there is always a need for methods of diagnosis which are improvements in terms of speed, reliability, and/or cost. The present invention provides an improved diagnostic method by using genetic engineering techniques to detect genetic sequences potentially coding for phenotypically characteristic proteins.

The genetic engineering techniques used relate to the recent advances in recombinant DNA technology which have facilitated the isolation of specific genes or parts thereof and their transfer to bacteria, yeast, plant, or animal cells and to the viruses that infect these organisms. The transferred gene material (or modified gene) is replicated and propagated as the transformed cell or viruses replicate.

The transfer and expression of genes or portions thereof between viruses, eukaryotes, and prokaryotes is possible because the DNA of all living organisms is composed of the same four nucleotides. The basic differences reside in the sequences in which the nucleotides appear in the genome of the organism. Specific nucleotide sequences, arranged in codons (nucleotide triplets), code for specific amino acid sequences. However, the coding relationship between an amino acid sequence and a DNA nucleotide sequence is essentially the same for all organisms.

Many recombinant DNA techniques employ transfer vectors. A transfer vector is a DNA molecule which contains genetic information which insures its own replication when transferred to a host microorganism strain. Plasmids are an example. "Plasmid" is the term applied to any autonomously replicating DNA unit which might be found in a microbial cell, other than the genome of the host cell itself. A plasmid is not genetically linked to the chromosome of the host cell. Plasmid DNAs exist as double stranded ring structures. A plasmid DNA ring may be opened and a fragment of heterologous DNA inserted and the ring reclosed. Thus, transfer vectors serve as a carrier or vector for an inserted fragment of heterologous DNA.

Transfer is accomplished by a process known as transformation. During transformation, host cells mixed with plasmid DNA incorporate into themselves entire plasmid molecules. Once a cell has incorporated a plasmid, under appropriate conditions the latter is replicated within the cell and the plasmid replicas are distributed to the daughter cells when the cell divides. Any genetic information contained in the nucleotide sequence of the plasmid DNA, under appropriate conditions, can be expressed as DNA, RNA, or protein in the host cell. Typically, a transformed host cell is recognized by its acquisition of traits carried on the plasmid, such as resistance to certain antibiotics. Any given plasmid may be made in quantity by growing a pure culture of cells containing the plasmid and isolating the plasmid DNA therefrom.

Restriction enzymes are also frequently used in these techniques. They are hydrolytic enzymes capable of catalyzing site-specific cleavage of DNA molecules. The locus of restriction enzyme action is determined by the existence of a specific nucleotide sequence. Such a sequence is termed the recognition site for the restriction enzyme. Since any DNA susceptible to cleavage by such an enzyme must contain the same recognition site, the same cohesive ends will be produced by the cleavage Therefore, it is possible to join heterologous sequences of DNA which have been treated with a restriction endonuclease to other sequences similarly treated. Restriction sites are relatively rare, but the general utility of restriction endonucleases has been greatly amplified by the chemical synthesis of double stranded oligonucleotides bearing the restriction site sequence Therefore, virtually any segment of DNA can be coupled to any other segments simply by attaching the appropriate restriction oligonucleotide to the ends of the molecule, and subjecting the product to the hydrolytic action of the appropriate restriction endonuclease, thereby producing the requisite cohesive ends.

Other methods for DNA cleavage, ligation, or for end sequence modification are also available. A variety of nonspecific endonucleases may be used to cleave DNA randomly. End sequences may be modified by creation of oligonucleotide tails of dA on one end and dT at the other, or a dG and dC, to create sites for joining without the need for specific linker sequences.

The term "expression" is used in recognition of the organism ordinarily does not make use of all of its genetically endowed capabilities at any given time. Even in relatively simple organisms such as bacteria, many proteins which the cell is capable of synthesizing are not synthesized, although they may be synthesized under appropriate environmental conditions. When the RNA that codes for a given protein is being synthesized by the organism, that RNA is said to be expressed. The RNA synthesis will eventually lead to the synthesis of the corresponding protein.

The use of these techniques in the present invention is described below.

SUMMARY OF THE INVENTION

A diagnostic method in accordance with the present invention includes the steps of preparing a gene probe which includes genetic sequences that potentially encode proteins which are phenotypically characteristic of myelogenous leukemia; annealing denatured DNA from the gene probe to RNA of a patient to be diagnosed; and determining whether hybridization occurs. "Gene probe" is used in this patent to mean a vector, either by itself or within a host, which includes the genetic sequences described above. DNA can be isolated from the gene probe and tested for hybridization with RNA of a patient. Hybridization between the two indicates that the same genetic sequences appear in the sample from the patient as in the probe. Since those genetic sequences potentially encode proteins that are phenotypically characteristic of certain leukemias, a positive result from the hybridization tests indicates that the patient may be suffering from one of those particular diseases. In one embodiment of the present invention, the gene probe includes genetic sequences that potentially encode proteins which are phenotypically characteristic of chronic myelogenous leukemia.

In particular, the present invention relates to methods of diagnosing myelogenous leukemia which include the steps of (a) immobilizing RNA from a cell sample on a substrate, and (b) subjecting the immobilized RNA to hybridization with a labelled probe which comprises a sequence which is localized to chromosome 8, and more specifically, 8pter→8q22, the sequence being complementary to a mRNA that is characteristically present in an abundance of at least 500 mRNA molecules/cell in a myelogenous leukemia cell, in order to determine if the characteristic mRNA is present in the sample cells. In a specific embodiment, this method can be used to diagnose chronic myelogenous leukemia (CML). The RNA from the sample cells can suitably be total RNA or cytoplasmic RNA.

The characteristic mRNA encodes a 93 amino acid protein (excluding the first methionine present on all initial translation products) and is present in CML mRNA at an approximate concentration of $1 \times 10^{10}$ molecules/$\mu$g of mRNA. The myeloid related sequence mRNA has between approximately 350 and 600 bases.

The present invention also concerns nucleic acid probes which comprise the above-described sequence. Such probes can suitably be used to aid in diagnosis of myelogenous leukemias.

One clone prepared using the methods of the present invention, designated C-A3 (ATCC No. 39868), has been studied with numerous different RNA sample. A myeloid-related sequence (mrs) contained in this clone potentially encodes a protein or proteins which are highly expressed in the chronic phase of both Ph[1]-positive and Ph[1]-negative CML, as well as in a Ph[1]-positive AML. Expression is reduced in lymphoblastic crisis of CML (L BC-CML) and is essentially absent in myeloblastic crisis of CML (M BC-CML). These results suggest that this probe may be useful in diagnosing Ph[1]-negative CML and in distinguishing M BC-CML from L BC-CML and Ph[1]-positive AML.

Nucleotide sequence analysis indicates that mrs encodes what is apparently a 98-amino acid protein that includes an 18-amino acid leader sequence (again excluding the first methionine present on all initial translation products). Hybridization of an mrs cDNA probe to a Southern blot made from somatic cell hybrid DNAs shows 100% concordance with human chromosome 8, thus indicating that mrs localizes to this chromosome.

When Southern blot hybridization was performed by using somatic cell hybrid DNAs harboring either a single 8q− or a single 21q+ chromosome from two different patients with M2-ANLL, a signal was only detected in the hybrid containing the 8q−(8pter→8q22::21q22.3→21qter) chromosome. In one particular embodiment of the present invention, the mrs is sublocalized to bands 8q21.1-23.

This mrs mRNA is predominantly expressed in promyelocytes, myelocytes, eosinophils, and basophils. Northern blot analysis indicates it is either completely absent or rare in poly(A+) RNAs from human muscle, intestine, liver, pancreas, and spleen as well as total RNAs from resting and phytohemagglutinin (PHA)-stimulated peripheral blood mononuclear cells.

The present invention should complement conventional laboratory techniques for diagnosing certain leukemias. It is possible that results of diagnostic tests in accordance with the present invention could be determined in as little as one day.

Another aspect of the present invention concerns a method of selecting at least one mRNA that is phenotypically characteristic of a particular malignancy. The method includes the steps of obtaining RNA from a patient suffering from a particular malignancy, preparing cDNAs corresponding to the RNA obtained, preparing a plurality of recombinant transfer vectors which each contain a cDNA insert from the cDNAs prepared, using the plurality of vectors to transform a plurality of hosts, subjecting the cDNA inserts in the plurality of transformed hosts to hybridization with labelled RNA, possibly in the form of cDNA, from another patient suffering from the same malignancy and with labelled RNA, again possibly in the form of cDNA, from nonmalignant tissue, and selecting at least one cDNA insert which exhibits minimal hybridization with the RNA from nonmalignant tissue and substantial hybridization with the RNA from the other patient suffering from the same malignancy. The existence of a strong hybridization signal with RNA taken from a patient suffering from the same malignancy indicates that the sequence being tested is one which is highly expressed in that malignancy. As a further way of selecting such a mRNA, the cDNA inserts can further be subjected to hybridization with labelled RNA, again possibly in the form of cDNA, from at least one other patient suffering from a different malignancy. The cDNA fragments that are selected should be ones that show minimal hybridization with the RNA of this additional patient suffering from a different malignancy.

DETAILED DESCRIPTION OF SPECIFIC EMBODIMENTS

The following is an example of how to prepare and use gene probes in accordance with the present invention. Those skilled in the art will recognize that modifications could be made that would achieve the same result.

I. Construction of a cDNA Library

A. RNA Extraction and Purification

Total RNA was isolated from a patient suffering from chronic phase, Ph[1]-positive CML, using the procedure described in Frazier, et al., "Efficient Extraction of RNA from Mammalian Tissue", Molecular and Cellular Biochemistry, 56:113–122 (1983). (This and the other publications cited in this patent are incorporated herein by reference.) The patient was male and had blood type O-positive. He exhibited the common 9:22 translocation in 100% of the metaphases recovered from his bone marrow. All stages of myeloid differentiation were represented in the sample utilized for library construction, with a preponderance of the leukocytes in the myelocyte or more mature categories.

A 195 ml sample with a cell count of $4.06 \times 10^8$/ml was collected by leukapheresis. The red blood cells were lysed with a solution containing 14 mM $NH_4Cl$, 17 mM Tris-HCL, pH 7.2, and the leukocytes were isolated by centrifuging. The pellets were extracted with 112 ml of a buffer solution consisting of 75 mM NaCl, 25 mM $Na_2EDTA$, 0.1% Sarkosyl NL-97 (ICN Pharmaceuticals, Inc., Plainview, N.Y.), and 10 mM Tris (pH 8.0), combined with 88 ml of phenol saturated with buffer. This mixture was then centrifuged for 20 minutes at 5000 rpm and 4° C. using a Sorvall GSA rotor.

The aqueous phase was removed and incubated with 10 µg/ml proteinase K (catalog no. 24568-10, E.M. Biochemicals, cals, Cincinnati, Ohio) for one hour at 37° C. The digests were then extracted with 50 ml of phenol saturated with the buffer solution described above and 50 ml of sevag solution (chloroform/isoamyl alcohol; 48:2, v/v). This mixture was centrifuged for 20 minutes at 5000 rpm and 4° C. in a GSA rotor. The aqueous phase was removed from the samples and the nucleic acid was precipitated with 2 volumes of 95% ethanol and 1/25 volume of 5 M NaCl.

The precipitates were collected by centrifugation, and then were resuspended in 45 ml of sterilized water and 90 ml of 4.5 M sodium acetate and placed overnight at −20° C. The centrifugation and resuspension steps were repeated until the sample was DNA free. After the final precipitation, the sample was resuspended in sterile $H_2O$.

Poly (A+) RNA was selected by oligo (dT) chromatography using essentially the procedures described in Munjaal et al., "Isolation and Characterization of Preproinsulin mRNA from Fetal Bovine Pancreatic Islets," Molecular and Cellular Endocrinology, 15:51–60 (1979). Two columns were set up with oligo (dT) cellulose Type III (Collaborative Research Corp., San Diego, Calif.). Both were washed with water and 0.1 N sodium hydroxide and equilibrated with a binding buffer solution which contained 10 mM Tris, 0.5 M sodium chloride, 1 mM EDTA, and 0.5% Sarkosyl, pH 7.5.

After the sample was heated to 68° C., the RNA was mixed with an equal volume of 2× binding buffer and passed through the columns. The mixture that passed through the columns was collected and run through again. The columns were then washed with binding buffer to remove unbound RNA. Elution of the bound RNA was performed with an elution buffer which contained 10 mM Tris, 1 mM EDTA, and 0.5% Sarkosyl pH 7.5. The columns were then washed extensively with elution buffer and equilibrated with binding buffer.

Poly (A+) RNA which was passed over a column once was heated to 68° C. for 5 minutes, added to an equal volume of 2× binding buffer, and repassed through the oligo dT column. Elution was done as before. Precipitation was caused by adding 2 volumes of 100% ethanol and 1/25 volume of 5 M sodium chloride, and holding this mixture at −80° C. for 1 hour. After thawing, the samples were centrifuged at 17,500 rpm for 30 minutes at 4° C. to separate supernatant from the pellets, using an HB-4 rotor.

B. Synthesis of Single Strand cDNA

Single strand cDNA with a $^3$H-dCTP (deoxycytidine triphosphate) tracer was prepared from 10 µg of the poly (A+) RNA in a 400 µl reaction containing 50 mM Tris-HCl, pH 8.3; 9 mM magnesium acetate; 50 mM potassium chloride; 20 mM dithiothreitol (DTT); 50 µCi $^3$H-dCTP (24.8 Ci/mmol); 750 µM each of dATP (deoxyadenosine triphosphate), dCTP dGTP (deoxyguanosine triphosphate), and dTTP (deoxythymidine triphosphate); 400 µM sodium pyrophosphate; 11.4 µg actinomycin D; 10 µg oligo $(dT)_{12-18}$ primer; and 180 units of reverse transcriptase (Life Sciences, St. Petersburg, Fla.) This mixture was incubated at 46° C. for 20 minutes, and was then adjusted to 0.3 N sodium hydroxide in a 30 µl volume, incubated at room temperature overnight to permit RNA hydrolysis, and then adjusted to pH 7.

C. Second Strand Synthesis

This synthesis generally followed the procedure described by Efstratiadis, et al., "Enzymatic In Vitro Synthesis of Globin Genes," Cell 7:279 (1976). The 40 µl reaction contained the single stranded cDNA; 50 µCi $^{32}$pdCTP as a tracer; 120 mM potassium phosphate buffer, pH 6.9; 10 mM magnesium chloride; 10 mM DTT, and 500 µM each dATP, dTTP, dCTP and dGTP; along with 22.5 units of *E. coli* DNA polymerase I holoenzyme. The reaction mixture was incubated at 15° C. for 6 hours and 15 minutes.

Single strand regions were removed by treatment with 50 units S1 nuclease (Miles Laboratories, Napersville, Ill.,) in a buffer containing 300 mM NaCl; 50 mM NaOAc, pH 4.5; and 1 mM $ZnCl_2$ at 37° C. for 30 minutes.

D. Recombination and Transformation pBR322 plasmid was used, which has the characteristics of resistance to tetracycline and ampicillin. The restriction enzyme PstI was used to cut the circular plasmid DNA inside the ampicillin resistant gene.

The plasmid DNA was then dG tailed after standard RNAse A treatment. Forty µ(3.36 µg) of the pBR, 20 µl of 1 M potassium cacodylate, 1 µl of bovine serum albumin (BSA) (50 μg/μl); 8 μl of 100 mM magnesium chloride; 1 μl of 100 mM BME (β-mercaptoethanol); 1 μl of 10 mM dGTP; 0.8 μl (20 units) of terminal deoxynucleotidyl transferase; and 28.2 μl of distilled water were mixed to give a total reaction volume of 100 μl. The mixture was incubated at 37° C. for 1.5 hours. Tail length was calculated by including a $^3$H-dGTP tracer.

The double stranded cDNA from the previous steps was dC tailed by mixing 10 μl of 1 M potassium cacodylate; 5 μl of 10 mM cobalt chloride; 1 μl of 5 mM dCTP; 1 μl of 50 mM BME; 25 ng of BSA; 14.75 μl of water; 14.75 μl of the DNA; and 1 μl (approximately 12 units) of terminal deoxynucleotidyl transferase, and incubating the mixture at 37° C. for 3.5 minutes. Tail length was estimated by including a $^3$H-dCTP tracer.

The dC tailed double stranded cDNA was annealed to the dG tailed pBR322, which had already been linearized at the PstI restriction site as described above. Equimolar amounts of the two (approximately 0.028 μg of the former and 0.47 μg of the latter; $1.67 \times 10^{-7}$ moles of each) were diluted to 125 μl in annealing buffer (300 mM NaCl; 1 mM EDTA; 10 mM Tris-HCl, pH 7.5). The mixture was incubated at 66° C. for 5 and ⅔ hours, then was allowed to cool to room temperature slowly overnight in a water bath.

*Escherichia coli* strain RRI cells were transformed by mixing the chimeric plasmid produced above with calcium treated cells, followed by 1.5 minute heat shock treatment at 42° C. This was followed by a five fold dilution with L-broth and incubation for 1 hour at 37° C. The solution was plated onto L-agar plates and transformed colonies were allowed to grow up overnight at 37° C. Supplementing the L-agar with 12.5 μl/ml tetracycline permitted selection of the colonies which had been transformed. After the initial transformation, supplementation with 50 μl/ml of ampicillin permitted detection of the ones which were ampicillin sensitive, and therefore had the cDNA insert. The colonies so selected were used as a "library" for screening.

II. Screening the cDNA Library

The colonies were grown for 8 to 12 hours at 37° C. on nitrocellulose filters placed on tetracycline-supplemented L-agar plates. The filters were then transferred to similar plates containing 200 μl/ml of chloramphenicol for an additional 12-16 hour incubation period. The filters were then denatured and fixed using the procedure described in Grunstein et al., "Colony Hybridization: A Method for the Isolation of Cloned DNA's that Contain a Specific Gene," Proc. Natl. Acad. of Sci. U.S.A., 72:3961 (1975), omitting the fixation steps described in that article from proteinase K treatment onward. A piece of Whatman's 3 MM paper was soaked with solutions of 0.5 M sodium hydroxide and 1.5 M sodium chloride, and then the filters were placed on top of the paper to soak. The filters were dried, soaked once again, dried again, and then soaked with paper that had been soaked in a 1.0 M Tris solution, pH 7.4. Finally, the filters were soaked on paper containing 1.0 M Tris, pH 7.4; 1.5 M NaCl. After further drying, the filters were baked for 3 to 6 hours at 68° C.

The filters were prehybridized in 400 ml of solution containing 120 ml of 20×SSC (1×SSC=0.15 M NaCl, 0.015 M Na$_3$ citrate), pH 7.0; 16 ml of 50×Denhardt's solution; and the balance distilled water.

Hybridization occurred in a solution containing 9 ml of 20×SSC, pH 7.0; 1.2 ml of 50×Denhardt's; 150 μl of 200 mM EDTA; 1.5 ml of 10% Sarkosyl; and distilled water to make a total volume of 30 ml. The filters were placed in bags, 4 filters per bag, with 10 ml of the hybridization solution and 50 μl of the radiolabelled single stranded cDNA.

The radiolabelled cDNA had been prepared by mixing 10 μl of homologous RNA (2.5 μg) with 2.5 μl of 1 M Tris-HCl, pH 8.3; 3.0 μl of oligo dT$_{12-18}$ primer (500 μl/ml); 4.0 μl of 100 mM magnesium acetate; 2.5 μl of the 1 M potassium chloride; 5.0 μl of 0.1 M DTT; 0.5 μl each of 50 mM dGTP, 50 mM dTTP, 50 mM dATP, and 5 mM dCTP; and 6.25 μl of actinomycin D (400 μl/ml). The reaction also contained 300 μCi of $^{32}$p-dCTP (S.A. 3000 Ci/mmole) which had been dried down and 2.5 μl of reverse transcriptase (22.5 units). Incubation was for 25 minutes at 46° C.

Approximately $1.0 \times 10^6$ radioactive counts were added per ml of hybridization solution. The mix was incubated at 68° C. overnight. After washing for 6 hours at 68° C. with 1×SSC; 0.5% Sarkosyl, the filters were rinsed with 1×SSC. The filters were then exposed to x-ray films for 1 to 3 days at −70° C. in the presence of intensifying screens.

Four hundred seventeen colonies out of a total of 1029 (40.5%) displayed a hybridization signal more intense than control colonies containing plasmid pBR322 without a cDNA insert, indicating that the recombinant plasmids which transformed the parent cell of those 417 colonies contained middle or highly repetitive RNAs from the CML patient. These 417 colonies were used for further screening.

This subset library was then screened against $^{32}$p-cDNA's transcribed from leukocyte poly (A+) RNAs of patients with chronic phase, Ph$^1$-positive CML, mixed blastic crisis CML (M BC-CML and L BC-CML), acute myelomonocytic leukemia (AMML), and human placenta. The screening procedure was largely as described above. Sixteen colonies of the 417 in the subset library showed little or no hybridization with the placenta and AMML-derived probes. The results for those 16 are shown in Table 1.

TABLE 1

HYBRIDIZATION INTENSITY OF SELECTED CML cDNA CLONES WITH $^{32}$P-cDNA FROM DIFFERENT TISSUES

| Clone | Homologous CML | Chronic Phase CML | Mixed M/L BC-CML | AMML | Human Placenta |
|---|---|---|---|---|---|
| C-A3 | ++ | ++ | − | +/− | − |
| C-A4 | ++ | ++ | − | − | − |
| C-B1 | ++ | + | + | − | +/− |
| D-D1 | ++ | ++ | − | +/− | − |
| E-B4 | ++ | ++ | − | +/− | +/− |
| E-D4 | ++ | − | − | − | +/− |
| E-E3 | ++ | − | + | +/− | +/− |
| E-F5 | + | − | + | − | +/− |
| E-H5 | ++ | + | − | − | − |
| F-F1 | + | ++ | ++ | − | − |
| G-H2 | + | + | + | − | +/− |
| G-H3 | + | + | − | − | − |
| H-E2 | ++ | + | − | − | +/− |
| H-G1 | + | − | − | +/− | − |
| J-E5 | + | + | − | +/− | − |
| J-F1 | ++ | + | − | +/− | − |

Plasmids isolated from 8 of the colonies listed in Table 1 were radiolabelled with $^{32}$p and hybridized to nitrocellulose filters (Northern Blots) containing total RNA extracted from normal and leukemic leukocytes. Filters containing immobilized RNA were prepared by size fractionating the RNA through agarose denaturing gels and transferring it to nitrocellulose paper. By utilizing a constant amount of RNA in the denaturing gels, it was possible to compare the relative message abundance of samples on the filters as well as to estimate the size of the RNA molecules with homology to the recombinant plasmid. Reutilization of the filters helped determine whether recombinants contained cDNA inserts transcribed from the same RNA molecules and provided evidence that lack of detectable signal was not due to degradation or incomplete transfer of the RNA. Plasmids containing homologous cDNAs would be expected to hybridize with RNAs of the same size and relative abundance on a given filter.

In the Northern Blot analysis, total RNA was isolated from peripheral blood leukocytes obtained by venapuncture of leukapheresis as described in Frazier et al., supra, or by utilizing a minor modification where DNA was removed by DNAse (Worthington) treatment. Plasmid was isolated from individual colonies and separated from cleared lysate by cesium chloride-ethidium bromide density ultracentrifugation. Nitrocellulose filters were prepared, prehybridized, hybridized, and washed essentially as described in Thomas, "Hybridization of Denatured RNA and Small DNA Fragments Transferred to Nitrocellulose," Proc. Natl. Acad. Sci. U.S.A., 77:5201 (1980), using 2-10 μg of glyoxylated total RNA from each sample.

The RNA samples were applied to vertical 1.2% or 1.5% agarose gels, electrophoresed for 8 hours at 50 volts, and transferred to nitrocellulose paper overnight. The filters were baked for 2 hours in a vacuum oven at 80° C., then prehybridized and hybridized with sheared calf thymus DNA. The plasmid was nick translated to high specific activity ($0.5-2.0 \times 10^8$ cpm/μg.) with [$^{32}$p]-dCTP and added to the hybridization solution at $2.00 \times 10^6$ cpm/ml. Initial filter washes were performed at room temperature with 2 final washes for 15 minutes each at 42° C. The filters were air dried, then exposed to x-ray film for 1 to 7 days at room temperature, −20° C., or −70° C. in the presence of intensifying screens.

The results indicated that 6 of the 8 plasmids tested in this manner represent RNA sequences preferentially expressed in the $Ph_1$-positive leukemias. Sequence G-H3 (approx. 1000 NT; "NT" is the number of nucleotide residues) was highly expressed in the M BC-CML and moderately expressed in one chronic phase CML. F-F1 (approx. 750 NT) was moderately expressed in L BC-CML and highly expressed in the chronic phase CMLs. E-B4 RNA (approx. 700 NT) was also highly represented in all chronic phase CMLs and the L BC-CML. D-D1 (approx. 1500 NT) was moderately expressed in all the Ph[1]-positive samples tested including both the samples in blastic crises. Clone C-A4 (approx. 720 NT) displayed low to moderate hybridization with the chronic phase CMLs. C-B1 failed to hybridize with any of the RNAs whereas H-G1 hybridized at low levels with all of them.

Because of the initial observation that the recombinant clone C-A3 represented sequences moderately transcribed in L BC-CML and highly expressed in all chronic phase CMLs, it was tested further. Total RNA was prepared from the peripheral blood leukocytes of a larger sampling of patients with various types of leukemias and used in additional hybridization experiments. The samples tested with C-A3 included four AMMLs, one AML, three ALLs, three CLLs, a Ph[1]-negative CML, a Ph[1]-positive AML, a myeloproliferative disorder (MPD) (Table 2, Sample 40a), eight Ph[1]-positive CMLs in chronic phase, one M BC-CML, one L BC-CML, and two different pools of normal peripheral blood leukocytes from a total of 24 donors. The MPD patient was considered distinguishable from Ph[1]-negative CML because the laboratory assay for leukocyte alkaline phosphatase (LAP) was normal or elevated rather than decreased.

No hybridization of C-A3 was detectable with filters containing 5-10 μg of total RNA from the normal RNAs, one AMML, the ALLs and one CLL after a 3 day exposure. A very faint signal could be seen with the M BC-CML, two CLLs, three AMMLs, and the AML (Table 2, Samples 19, 23, 24, 32, 33, 34, and 37). Intense hybridization was evident after a 1 day exposure of the filters with only 2 μg of the total RNA from the eight Ph[1]-positive CML patients in chronic phase, the Ph[1]-negative CML, and the Ph[1]-positive AML. A moderate signal was detectable in the patient with L BC-CML where a white cell differential disclosed that 31% of the cells were blasts. There was no detectable hybridization with the ALL, the MPD patient, the myeloblastic crisis (76% blasts) and the normal RNAs. Multiple transcript sizes were present in some of the samples. Expression did not appear to correlate with clinical or laboratory data or the therapy status.

Since total RNA extraction requires numerous cells and does not specifically select for cytoplasmic RNA, on 11 of the samples utilized for total RNA extraction as well as on several additional ones, a modification of the procedure for preparation of cytoplasmic RNA from small numbers of leukocytes described in White et al., "Simple Analysis of Relative mRNA levels in Multiple Small Cell or Tissue Samples," J. Biol. Chem. 257:8569 (1982), was used. RNA was directly blotted onto nitrocellulose paper, bound and then hybridized with radiolabelled probe C-A3.

In this procedure, leukocytes were isolated from whole peripheral blood or leukapheresis specimens by pelleting the cells and lysing the erythroid elements. Cytoplasmic RNA was then prepared using a modification of the procedure described in White, supra. $5 \times 10^6$ cells were resuspended in 43 μl of the cold buffer consisting of 10 mM Tris-HCl and 1 mM EDTA, pH 8.0. One μl each of 100 mM DTT and RNAsin (25 units/μl, Biotec) were added to inhibit RNAse activity. Cells were enucleated by adjusting to 0.5% with 5.0% NP-40 (Shell Corp.), incubating 5 minutes at 0° C., and pelleting the nuclei. The cytoplasm supernatant was mixed with an equal volume of 12>SSC/14.8% formaldehyde incubated at 65° C. for 30 minutes and then stored at −70° C. Filters were prepared by diluting 5 μl of the sample to 150 μl with 15×SSC, applying the RNA by vacuum filtration to nitrocellulose soaked in 15×SSC using a Minifold II slot blotter system (Schleicher and Schuell) and baking under a vacuum for 2 hours at 80° C. Prehybridization, hybridization, and washes were performed as described for Northern Blots.

Consistent with the results obtained from the glyoxal gel experiments, the peripheral blood samples from the Ph[1]-positive AML, the L BC-CML and 11 of 12 chronic phase CMLs were positive after a brief exposure of the filter for autoradiography. The negative CML sample (Table 2, Sample 17) was obtained from a treated patient who had a blood differential and white count resembling that of a normal individual, although the LAP value was still decreased and Ph[1]-positive metaphases were present in the bone marrow. Two other samples of myeloid origin were also positive. One was a diploid AML (Table 2, Sample 38) with 94% blast cells in the differential and a normal LAP value. The other was the later of 2 samples obtained from the MPD patient (Table 2, Sample 40b). A longer exposure of the filter failed to reveal a signal with the other samples tested with the exception of two CLLs and one ALL (Table 2, Samples 25, 26 and 28). This ALL patient presented with 10% Ph[1]-positive hyperdiploid cells in the marrow prior to therapy.

The results of the testing with peripheral blood samples is summarized in Table 2. In addition to the abbreviations already defined, AMoL (acute monocytic leukemia) is used in the table.

TABLE 2

PERIPHERAL BLOOD SAMPLES

| Sample No. | Diagnosis | Result with C-A3 |
|---|---|---|
| 1 | CML | POS |
| 2 | CML | POS |
| 3 | CML | POS |
| 4 | CML | POS |
| 5 | CML | POS |
| 6 | CML | POS |
| 7 | CML | POS |
| 8 | CML | POS |
| 9 | CML | POS |
| 10 | CML | POS |
| 11 | CML | POS |
| 12 | CML | POS |
| 13 | CML | POS |
| 14 | CML | POS |
| 15 | CML | POS |
| 16 | CML | POS |
| 17 | CML | NEG |
| 18 | CML | POS |
| 19 | M BC-CML | +/− |
| 20 | M/L BC-CML | NEG |
| 21 | L BC-CML | POS |
| 22 | L BC-CML | POS |
| 23 | CLL | +/− |
| 24 | CLL | +/− |
| 25 | CLL | +/− |
| 26 | CLL | +/− |
| 27 | CLL | NEG |
| 28 | ALL | +/− |
| 29 | ALL | NEG |
| 30 | ALL | NEG |
| 31 | ALL | NEG |
| 32 | AMML | +/− |
| 33 | AMML | +/− |
| 34 | AMML | +/− |
| 35 | AMML | NEG |
| 36 | AML | POS |
| 37 | AML | +/− |
| 38 | AML | POS |
| 39 | AMoL | NEG |
| 40a | MPD | NEG |
| 40b | MPD | POS |
| 41 | normal | NEG |
| 42 | normal | NEG |
| 43 | normal | NEG |
| 44 | normal | NEG |
| 45 | normal | NEG |
| 46 | normal | NEG |

Results obtained with the bone marrow samples were less dramatic, as can be seen from Table 3.

TABLE 3

| BONE MARROW SAMPLES | | |
|---|---|---|
| No. | Diagnosis | C-A3 |
| 1 | CML | POS |
| 2 | CML | POS |
| 3 | CML | POS |
| 4 | CML | POS |
| 5 | CML | POS |
| 6 | CML | POS |
| 7 | CML | POS |
| 8 | CML | POS |
| 9 | CML | NEG |
| 10 | M BC-CML | NEG |
| 11 | CLL | POS |
| 12 | CLL | +/− |
| 13 | MPD | POS |
| 14 | MPD | +/− |
| 15 | normal | POS |
| 16 | normal | POS |
| 17 | normal | POS |
| 18 | normal | +/− |

None of the negative results were due to degradation since all samples showed positive hybridization with different RNA probes.

Certain points are significant about the results of the tests with the C-A3 probe. First, more than one transcript size was detected in some of the samples. This may simply reflect the fact that total cellular RNA was utilized for these studies and the larger band is a nuclear RNA precursor of the processed mRNA. Second, while it was derived from a cDNA library made from a Ph[1]-positive CML patient, the hybridization profile of a Ph[1]-negative CML patient (Table 2, Sample 18) is similar to that found with the Ph[1]-positive CMLs. This provides molecular evidence for the phenotypic similarity of different CML populations. One of the C-A3 positive CML specimens utilized in the studies (Table 2, Sample 3) contained a complex translocation involving chromosomes 9, 11, 22, and two of the samples which were either C-A3 negative or only faintly positive (Table 2, Samples 30 and 32) had cytogenetic abnormalities involving the long arms of chromosome 9. These combined data imply that the problem of C-A3 expression could be more complex than a simple correlation with gross chromosomal changes. The possibility remains, however, that similar changes have occurred in the DNA of C-A3 positive patients which are only detectable at the molecular level.

An examination of the differentials and white blood cell counts of the samples shows that C-A3 expression is unlikely to be solely related to the presence of immature myeloid elements although these cells are likely to be capable of producing the C-A3 message. Two specimens which contained immature myeloid cells (other than blasts) failed to produce a detectable signal on autoradiograms (Table 2, Sample 40a; Table 3, Sample 9). Additionally, some of the samples which produced faint positives with clone C-A3 did not contain immature myeloid cells (Table 2, Samples 24–26) which suggests that cells other than those from the myeloid lineage can produce this mRNA. Since the genetic defect in CML is thought to occur in a multipotent stem cell, it is not surprising that low level transcription of C-A3 sequences can occur in multiple cell types. However, it appears that the highest transcription levels occur in CML, specifically in the chronic phase.

The clinical data on the patient from which Samples 40a and 40b in Table 2 were taken is notable since the second sample (40b) was positive. When the patient was first examined, the cytogenetic data indicated a dividing diploid population, the LAP was elevated (265) and although the marrow was suggestive of CML, the diagnosis was not definite. On a follow-up visit 12 months later, the dividing cell population was still diploid, the LAP was normal, and mild splenomegaly was noted. At this time, sample 40a was obtained from a therapeutic white cell depletion. This sample was negative for expression of C-A3. Five months later the patient returned with symptoms of gross splenomegaly and newly developed hepatomegaly. Although the LAP was still normal (177), standard therapy for CML was begun since the disease was becoming more aggressive. A sample obtained prior to initiation of therapy was found to be positive for C-A3 message. Two weeks later, the LAP value had dropped significantly (to 97) although it was still within our normal laboratory values. The data suggests that the patient had a developing $Ph^1$-negative CML. It appears to be highly significant that the expression of clone C-A3 could be correlated with the course of this disease.

A detectable difference was found in the C-A3 levels of blast crisis CML patients. Five patients were studied after entering blast crisis: two with L BC-CML, two with M BC-CML and one mixed crisis patient with both lymphoblasts and myeloblasts. Surprisingly, the patients with M BC-CML and the mixed crisis patients had significantly lower levels of C-A3 than the patients with L BC-CML. While additional blast crisis samples need to be studied, these results indicate that C-A3 represents an additional means of testing for differences between two seemingly similar populations of cells. This is important since the prognosis and therapy for M BC-CML and L LB-CML patients differ.

Additionally, it was found that a patient with $Ph^1$-positive AML had high levels of C-A3, whereas the marrow of a "poor prognosis" CML patient (Table 3, Sample 9) was negative. It is possible that C-A3 expression reflects an inherent state of the myeloid leukemia cells which is predictive for patient response to common therapy regimens.

The nucleotide sequence of mrs was determined as follows.

The dideoxy-chain termination method of sequencing was performed on mrs cDNAs subcloned from their parental plasmid vectors into derivatives of bacteriophage M13. Briefly, plasmids were digested with various restriction enzymes (according to the manufacturer's instructions), and the resulting DNA fragments were inserted into the artificial linker sites of the M13 derivatives. After transformation into the appropriate bacterial host (either JM-101 or JM-105), single-stranded bacteriophage DNAs were prepared from white plaques formed in the presence of isopropyl-$\beta$-D-thiogalactopyranoside and 5-bromo-4-chloro-3-indolyl-$\beta$-D-galactopyranoside. The cDNA inserts were then partially sequenced (C-track analysis) to identify candidate clones for complete sequencing (four-track analysis).

To C-track subclones, primer (15-mer or 17-mer, Pharmacia Laboratories, Piscataway, N.J.) was annealed with a single-stranded DNA template and extended through the cDNA insert by using Escherichia coli DNA polymerase I Klenow fragment in a buffered reaction mixture containing 24.5 $\mu$mol/L each of dATP, dGTP, and dTTP; 1.65 $\mu$mol/L dCTP; and 25.7 $\mu$mol/L dideoxy-CTP with [$^{32}$P] dCTP (3,000 Ci/$\mu$mol, Amersham Corp., Arlington Heights, Ill.) as a tracer. After a 15-minute incubation at room temperature, 0.2 vol of chase solution (2.5 $\mu$mol/L each of dATP, dCTP, dGTP, and dTTP) was added, and the incubation was continued for an additional 15 minutes. The reaction was stopped with the addition of an equal volume of dye mix (96% formamide, 0.1% bromophenol blue, 0.1% xylene cyanol, and 10 $\mu$mol/L $Na_2EDTA$), and the randomly terminated products were size-fractionated by electrophoresis through an ultrathin (0.3 mm) 5% polyacrylamide/48% urea denaturing gel.

To perform four-track analysis, four separate annealing reactions were set up (for each subclone). Similar to C-track analysis, primers were extended through the cDNA inserts by using Klenow fragment in buffered reactions containing [$^{32}$P]-dCTP as a tracer; however, incubations were carried out at 30° C. rather than room temperature, and the concentrations of deoxynucleotides and dideoxynucleotides varied in each reaction. In all assays the concentration of dCTP was 6.4 $\mu$mol/L. For the dCTP analysis, dATP, dGTP, and dTTP were 26.0 $\mu$mol/L each, and dideoxy-CTP was 27.3 $\mu$mol/L. In the dATP assay, dGTP and dTTP were 35.0 $\mu$mol/L each, dATP was 3.5 $\mu$mol/L, and dideoxy-ATP was 182.0 $\mu$mol/L. For dGTP analysis, the concentrations of dATP, dTTP, dGTP, and dideoxy-GTP were 35.0, 35.0, 3.5 and 182.0 $\mu$mol/L, respectively, whereas for analysis of dTTP the concentrations of dATP, dGTP, dTTP, and dideoxy-TTP were 35.0, 35.0, 3.5, and 182.0 $\mu$mol/L. As with C-track analysis, chase solution was added after 15 minutes, the incubations were continued for an additional 15 minutes, dye mix was added, and the reaction products were size-fractionated on an ultrathin polyacrylamide/urea denaturing gel.

Figure 1:
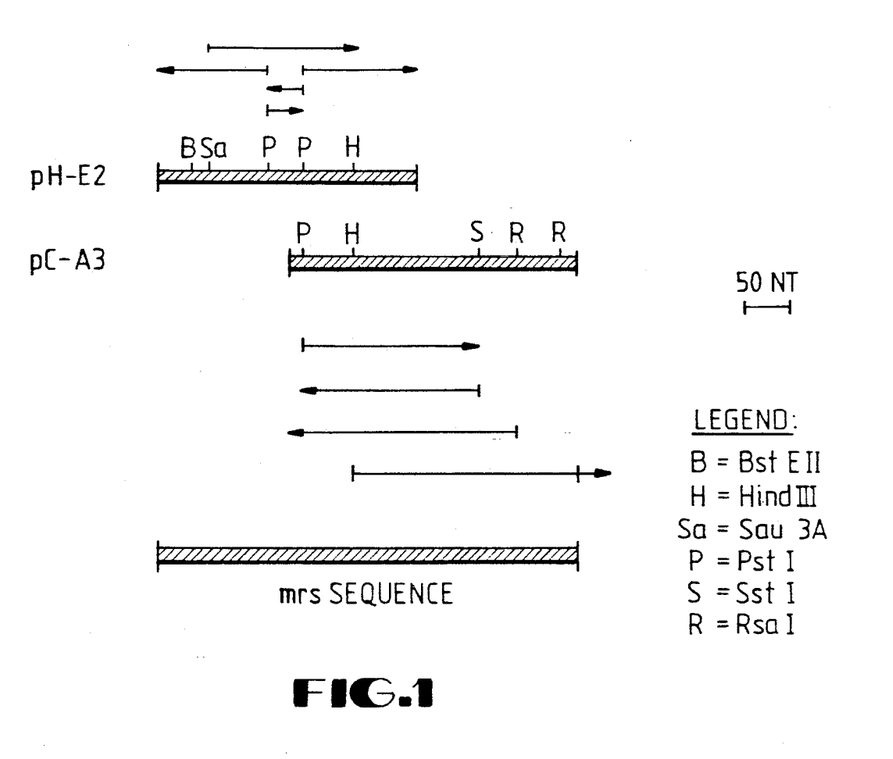
FIG. 1 is a restriction map and a diagram of the sequencing strategy of the CML-derived mrs cDNA clones.

Because of a deletion in the pBR322 parent plasmid, the insert in the original mrs cDNA clone (pC-A3) was linearized but not excisable by PstI digestion. To overcome this problem, pC-A3 was either digested with RsaI or a combination of PstI and RsaI. The resulting fragments were ligated into bacteriophage M13mp8 digested with either SmaI alone or SmaI in combination with PstI. After transformation, bacteriophage DNAs were isolated and subjected to sequencing. After the nucleotide sequence was examined, a strategy was developed for resequencing the pC-A3 insert in overlapping fragments (FIG. 1). The PstI/SstI fragment was isolated by using polyacrylamide gel electrophoresis and directionally subcloned into bacteriophage M13mp18 and M13mp19. A HindIII fragment encompassing part of the cDNA and part of the pBR322 vector was also isolated and subcloned into the HindIII site of M13mp18.

The pC-A3 insert contained a poly(A) track preceded by a polyadenylation signal, which indicated that it represented the 3' end of the mrs message; however, because the insert was smaller than the estimated length of the mRNA from Northern blot analysis, it did not contain a full-length mrs cDNA. To identify other clones that might contain sequences from the 5' end of mrs, the PstI/SstI fragment subcloned into M13mp19 was radiolabeled and hybridized to a Southern blot made from 16 recombinant plasmids that were originally isolated as potentially representing mRNAs over expressed in CML. Six of these clones (including pC-A3) hybridized with the probe. The PstI restriction digest pattern of clone pH-E2 suggested that it contained sequences that were not present in pC-A3. For sequencing, pH-E2 was digested with PstI and ligated with PstI-restricted M13mp18. Two different recombinant phase-exhibiting poly(C) tracks were identified and fully sequenced. One contained sequences identical to the 5' end of pC-A3; the other was unique. To sequence across the internal PstI site, pH-E2 was digested with both Sau3A and HindIII, and the cDNA fragment was into M13mp19 cleaved with BamHI and HindIII. Because the sequencing indicated that pH-E2 contained a small internal PstI fragment (FIG. 1), the plasmid was redigested with PstI, and two different clones lacking poly(C) tails were analyzed.

Figure 2:
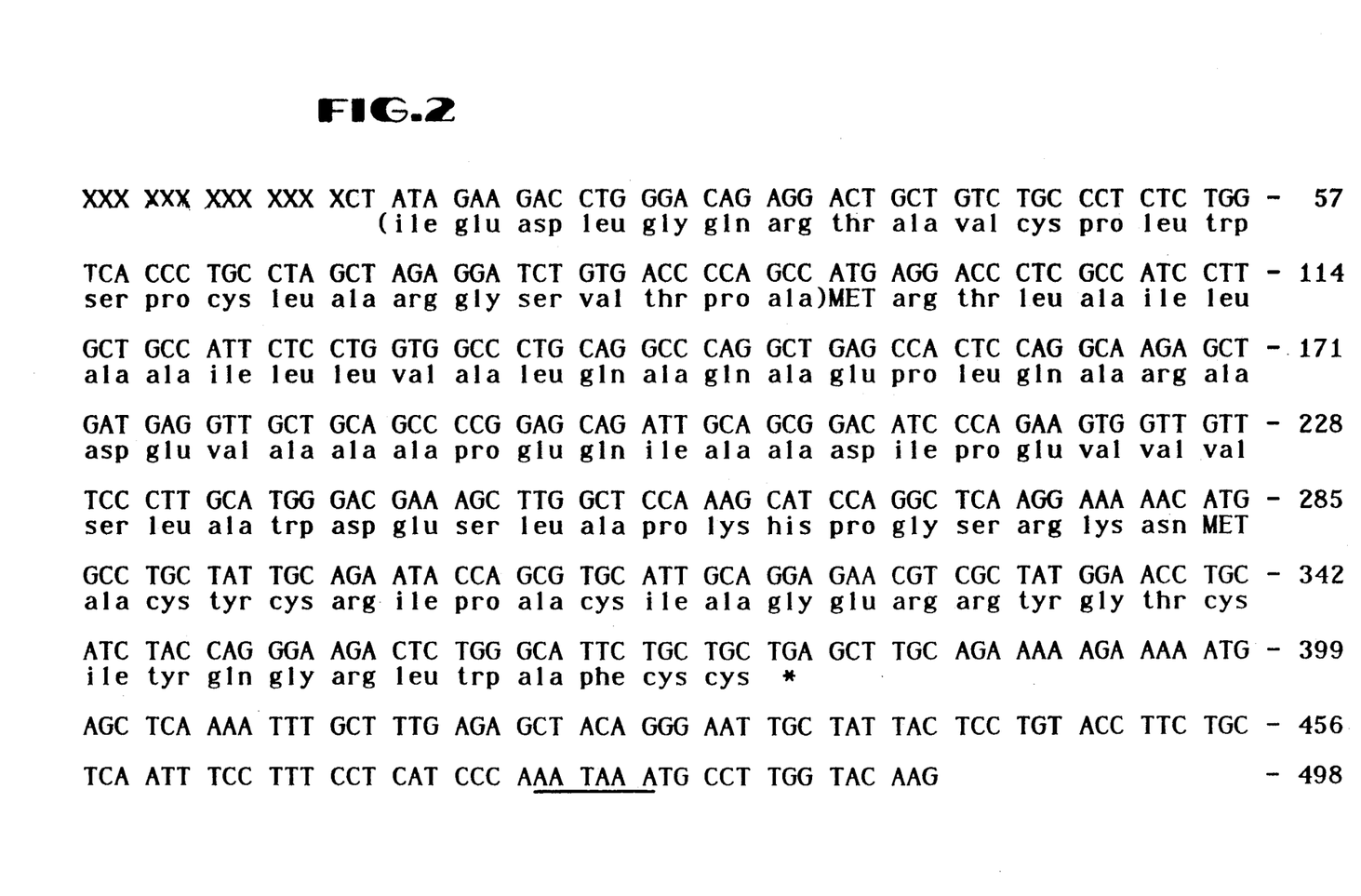
FIG. 2 is the nucleotide sequence and predicted protein sequences from the CML-derived mrs cDNA. Thirteen unknown nucleotides at the 5' end are depicted by X's. The derived amino acid sequence found before the first ATG is enclosed in parentheses, and the termination codon is indicated by an asterisk. The underlined nucleotides correspond to the consensus signal sequence for polyadenylation.

The combined pC-A3 and pH-E2 sequences produced an mrs cDNA 485 nucleotides long (FIG. 2). To determine whether nucleotide sequences were still missing from the 5' end, primer extension analysis was performed. A radiolabeled, single-stranded primer was generated from sequences spanning the PstI/BstEII fragment at the 5' end of the pH-E2 cDNA insert. This primer was annealed with CML poly(A+)RNA and extended by using reverse transcriptase. After hydrolysis of residual RNAs, the extended product was sized on a polyacrylamide/urea sequencing gel. The results of this experiment indicated that the mrs mRNA from CML cells contains an additional 13 nucleotides at the 5' end (FIG. 2).

The first AUG(ATG) triplet encountered in mrs occurs at nucleotide 94. It is followed by an open reading frame that is 93 amino acids long (FIG. 2) and begins with a string of 18 amino acids that resembles other leader sequences and their cleavage sites. Because the functional initiation codon of a protein sequence is generally encoded by the most 5' AUG triplet of the mature mRNA, this peptide is likely to represent the mrs protein. The nucleotides surrounding this AUG triplet match the consensus sequence for translation, which makes this an even stronger candidate for the initiation of translation. However, it is conceivable that another AUG is present in the 13 nucleotides at the 5' end of the mrs sequence. An open reading frame is found in alignment with the nucleotides preceding the AUG triplet at nucleotide 94, and the 93 amino acid polypeptide may actually be part of a larger protein.

To localize mrs. a Southern blot of EcoRI-digested DNAs from a rodent/human somatic cell hybrid panel was prepared and probed with the PstI/SstI fragment of pC-A3 subcloned into M13mp18. Hybridization indicated perfect concordance with hybrids containing human chromosome 8, as shown in Table 4 and FIG. 3, thereby localizing mrs to this chromosome.

Figure 3:
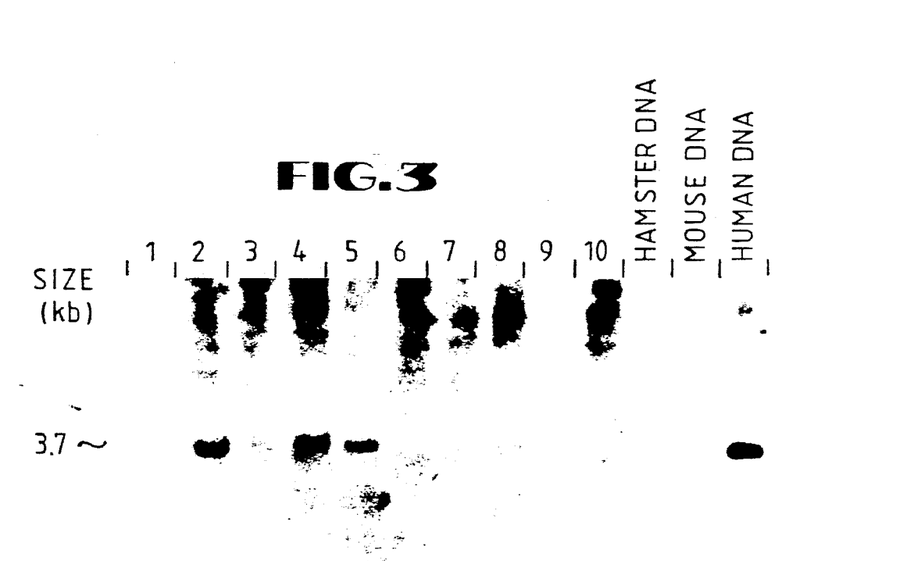
FIG. 3 shows the results of Southern blot analysis using somatic cell hybrid DNA's.

Somatic cell hybrids were made by fusion of rodent cells (mouse L cells, hamster lung fibroblasts, or Chinese hamster ovary [CHO] cells) with either human skin fibroblasts, mononuclear leukocytes, or lymphoblasts. Multiple clones were selected for expansion and subjected to karyotype analysis to determine which human chromosomes had been retained. DNAs from selected hybrids, rodents, and humans were isolated; digested to completion with EcoRI, BamHI, or HindIII according to the manufacturer's instructions; size-fractionated by electrophoresis through a 0.8% agarose gel; and transferred to a nylon membrane filter (Zetabind, AMF-Cuno, Meriden, Conn.; or Nytran, Schleicher & Schuell, Keene, N.H.) for Southern blot analysis. Prehybridization and hybridization were performed as described by Patel et al., "Organization of the HPRT Gene and Related Sequences in the Human Genome", Somatic Cell Mol. Genet. 10–483 (1984), by using [$^{32}$P]-radiolabeled cDNA probes made from either an M13 subclone (C-5-3) harboring the PstI/SstI fragment of mrs or the pBR322-derived plasmids pC-A3 or pH-E2. Radiolabeled C-5-3 was made by annealing primer with single-stranded template DNA and then extending with Klenow fragment in the presence of dATP, dGTP, dTTP, and [$^{32}$P]-dCTP. Plasmids were radiolabeled with [$^{32}$P]-dCTP by using the oligolabeling method.

TABLE 4

CHROMOSOME CONTENT OF SOMATIC CELL HYBRIDS AND THE HYDRIDIZATION PATTERN WHEN USING mrs

| Hybrids | | | | | | | | | | | |
|---|---|---|---|---|---|---|---|---|---|---|---|
| 1 | 2 | 3 | 4 | 5 | 6 | 7 | 8 | 9 | 10 | Chromosome | Discordance (%) |
| Human chromosome content | | | | | | | | | | | |
| − | + | − | − | − | − | − | + | − | − | 1 | 40 |
| − | − | − | − | + | + | +* | + | − | − | 2 | 60 |
| + | + | + | + | + | + | + | + | − | − | 3 | 40 |
| + | + | + | − | + | + | − | − | − | − | 4 | 30 |
| + | + | − | + | − | + | − | − | − | − | 5 | 40 |
| + | + | − | + | − | + | + | − | − | − | 6 | 50 |
| − | − | − | + | + | − | + | + | + | +/− | 7 | 60 |
| − | + | +/− | + | + | − | − | − | − | − | 8 | 0 |
| − | + | − | ++ | + | − | − | + | − | − | 9 | 20 |
| − | − | − | − | + | + | + | + | − | − | 10 | 50 |
| + | + | − | + | + | + | + | + | − | + | 11 | 60 |
| + | − | − | + | + | − | − | − | + | − | 12 | 40 |
| − | − | − | + | − | − | + | + | − | + | 13 | 60 |
| + | − | − | + | + | − | − | − | − | − | 14 | 30 |
| + | − | +/− | + | + | − | − | − | +ƒ | − | 15 | 30 |
| + | − | + | − | + | + | − | + | − | − | 16 | 50 |
| + | − | − | ++ | − | − | − | − | +ƒ | − | 17 | 50 |
| + | − | − | − | − | + | − | + | − | + | 18 | 80 |
| − | + | + | − | − | + | − | − | − | − | 19 | 30 |
| − | + | − | + | + | − | + | − | + | − | 20 | 30 |
| + | + | + | + | − | + | − | + | − | − | 21 | 40 |
| + | − | − | − | − | + | + | − | − | + | 22 | 80 |
| + | + | + | − | + | + | + | + | − | + | X | 60 |
| − | − | − | − | − | + | − | − | − | − | Y | 50 |
| mrs hybridization pattern | | | | | | | | | | | |
| − | + | + | + | + | − | − | − | − | − | | |

Hybrids 1 to 10 correspond to the previously described hybrids C₁1A. 1.2, 1.4, MH-18, 8.2, 16.1, MR2.2, MR5.11, SA-5, and MR7.11, respectively. Plus/minus (+/−) indicates that only 20% of the metaphase cells contain this chromosome.
*Contains fragment 2p only.
+In the rearrangement 9qter→9q12::17p11→17qter.
ƒIn the rearrangement 15qter→15q15::17p13→17qter.

TABLE 5

Sublocalization of mrs by Using Somatic Cell Hybrids

| Hybrid | Human Chromosome Content | | | Hybridization Pattern | |
|---|---|---|---|---|---|
| | 8 | 8q−* | 21q+ | pC-A3 | pH-E2 |
| 8;21/6B-12 ∫ | + | − | − | + | + |
| 13b1S816-10-3 | − | + | − | + | + |
| 21-8Ab5-23a[20] | − | − | + | − | − |

*8pter→8q22::21q22.3→21qter.
+21pter→21q22.3::8q22→8qter.
∫Hybrid 8;21/6B-12 has not been previously cited in a publication.

Southern blot analysis was also performed on CHO/human somatic cell hybrid DNAs containing either a single chromosome 8, 8q−, or 21q+ chromosome. Hybrids were made from two different M2-ANLL patients who each displayed an 8;21 translocation. A hybridization signal was detectable in somatic cell hybrids containing either a single chromosome 8 or a single 8q− (8pter→8q22::21q22.3→21qter) chromosome, whereas no signal was detectable in the hybrids containing a single 21q+ (21pter→21q22.3::8q22→8qter) chromosome, as shown in Table 5. Since no hybridization was detected with DNAs from the hybrids containing the 21q+ chromosome, in a second patient with M2-ANLL, mrs sequences do not move to chromosome 21.

The abundance of mrs transcripts in cytoplasmic RNAs from CML cells is believed to be approximately 500–2500 mRNA molecules/cell. It is possible that the majority of the mrs transcripts are in a small subset of the leukocyte population at an abundance greater than that listed above. The mrs content in the total cellular RNAs isolated from a Ph+ acute myeloblastic leukemia (AML), normal BM, and CML leukocytes ranged from approximately 25 to 235 pg/µg RNA. In a CML poly($A^{30}$)RNA sample the mrs content was approximately 3,500 pg/µg mRNA, or $1 \times 10^{10}$ molecules/µg of mRNA. Assuming that the average poly (A+) RNA molecule in a total cellular RNA preparation is 4,000 nucleotides long, there is an estimated $4.6 \times 10^{11}$ molecules/µg of RNA. Therefore, by calculation, mrs comprises approximately 2.2% of the RNA.

The preceding description is intended to illustrate the present invention. It is not intended to describe all possible embodiments of the invention.

We claim:

1. A nucleic acid probe having a sequence consisting essentially of that found in the transformed E. coli which is designated ATCC no. 39868 and which encodes a protein for which the corresponding mRNA is highly expressed in chronic myelogenous leukemia.

2. A nucleic acid molecule consisting essentially of the sequence beginning at the 5' end:

```
ATG AGG ACC CTC GCC ATC CTT GCT GCC ATT CTC CTG GTG GCC
CTG CAG GCC CAG GCT GAG CCA CTC CAG GCA AGA GCT GAT GAG
GTT GCT GCA GCC CCG GAG CAG ATT GCA GCG GAC ATC CCA GAA
GTG GTT GTT TCC CTT GCA TGG GAC GAA AGC TTG GCT CCA AAG
CAT CCA GGC TCA AGG AAA AAC ATG GCC TGC TAT TGC AGA ATA
CCA GCG TGC ATT GCA GGA GAA CGT CGC TAT GGA ACC TGC ATC
TAC CAG GGA AGA CTC TGG GCA TTC TGC TGC
```

3. A nucleic acid molecule consisting essentially of the sequence, beginning at the 5' end:

```
CTG CAG GCC CAG GCT GAG CCA CTC CAG GCA AGA GCT GAT GAG
GTT GCT GCA GCC CCG GAG CAG ATT GCA GCG GAC ATC CCA GAA
GTG GTT GTT TCC CTT GCA TGG GAC GAA AGC TTG GCT CCA AAG
CAT CCA GGC TCA AGG AAA AAC ATG GCC TGC TAT TGC AGA ATA
CCA GCG TGC ATT GCA GGA GAA CGT CGC TAT GGA ACC TGC ATC
TAC CAG GGA AGA CTC TGG GCA TTC TGC TGC
```

* * * * *

UNITED STATES PATENT AND TRADEMARK OFFICE
CERTIFICATE OF CORRECTION

PATENT NO. : 5,066,792

DATED : Nov. 19, 1991

INVENTOR(S) : Grady F. Saunders et al

It is certified that error appears in the above-identified patent and that said Letters Patent is hereby corrected as shown below:

At column 18, line 7, of the patent, "$A^{30}$" should instead read --$A^{+}$--.

In claim 2, column 18, lines 23-24, the phrase "molecule consisting essentially of the sequence" should instead read --probe, which consists essentially of a vector containing a nucleic acid sequence having no more than 600 bases comprising,--.

In claim 3, column 18, line 35, the phrase "molecule consisting essentially of the sequence" should instead read --probe, which consists essentially of a vector containing a nucleic acid sequence having no more than 600 bases comprising--.

Signed and Sealed this

Thirteenth Day of April, 1993

Attest:

STEPHEN G. KUNIN

*Attesting Officer*     *Acting Commissioner of Patents and Trademarks*